US008449614B2

United States Patent
Ferree

(10) Patent No.: US 8,449,614 B2
(45) Date of Patent: May 28, 2013

(54) SUTURES FOR USE IN THE REPAIR OF DEFECTS IN THE ANULUS FIBROSUS

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 1178 days.

(21) Appl. No.: 11/635,829

(22) Filed: Dec. 7, 2006

(65) Prior Publication Data

US 2007/0135920 A1   Jun. 14, 2007

Related U.S. Application Data

(60) Provisional application No. 60/748,518, filed on Dec. 8, 2005.

(51) Int. Cl.
*A61F 2/44* (2006.01)
(52) U.S. Cl.
USPC ........................................ 623/17.16
(58) Field of Classification Search
CPC ............................................. A61F 2/44
USPC .............. 606/60, 246, 263, 279, 280, 70, 71, 606/281, 283–286, 300, 301, 86 R, 151, 228, 606/232; 623/13.14, 17.11–17.13, 17.16, 623/23.39, 23.52, 23.54, 23.58, 23.59
See application file for complete search history.

(56) References Cited

U.S. PATENT DOCUMENTS

| 4,452,245 | A | * | 6/1984 | Usher | 606/151 |
| 5,665,112 | A | * | 9/1997 | Thal | 606/234 |
| 6,248,106 | B1 | | 6/2001 | Ferree | |
| 6,371,990 | B1 | | 4/2002 | Ferree | |
| 6,423,065 | B2 | | 7/2002 | Ferree | |
| 6,592,625 | B2 | | 7/2003 | Cauthen | |
| 6,652,585 | B2 | | 11/2003 | Lange | |
| 6,878,167 | B2 | | 4/2005 | Ferree | |
| 7,201,774 | B2 | | 4/2007 | Ferree | |
| 7,695,501 | B2 | * | 4/2010 | Ellis et al. | 606/281 |
| 2004/0234576 | A1 | * | 11/2004 | Martin et al. | 424/426 |
| 2005/0245932 | A1 | * | 11/2005 | Fanton et al. | 606/72 |

* cited by examiner

*Primary Examiner* — Eduardo C Robert
*Assistant Examiner* — David Comstock
(74) *Attorney, Agent, or Firm* — Pandiscio & Pandiscio

(57) ABSTRACT

Methods and devices for fixing a defect in a vertebral disc of a patient. One method includes providing first, second, third, and fourth sutures. The first and second sutures are fastened to a vertebra cranial to the vertebral disc at first and second locations, respectively. The third and fourth sutures are fastened to a vertebra caudal to the vertebral disc at third and fourth locations, respectively. A device, such as a mesh device, is positioned adjacent the defect. The first, second, third, and fourth sutures are then positioned against the device, on the side of the device opposite of the defect. Tension is then applied to the first, second, third, and fourth sutures. Each of the first, second, third, and fourth sutures are then attached to at least one of the first, second, third, and fourth sutures, thereby holding the device adjacent the defect.

6 Claims, 7 Drawing Sheets

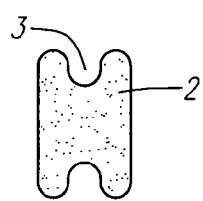 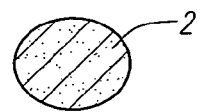
FIG. 1A                FIG. 1B
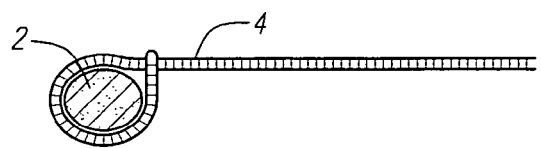
FIG. 1C
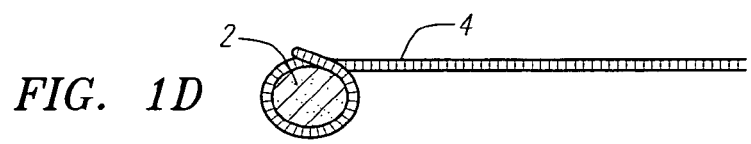
FIG. 1D
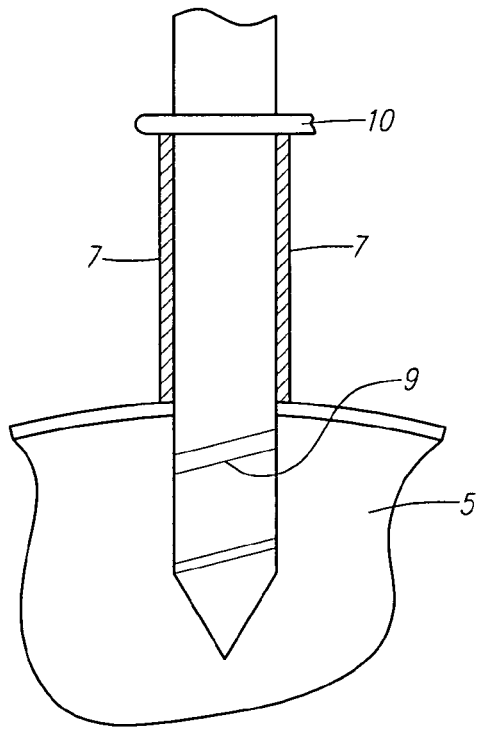 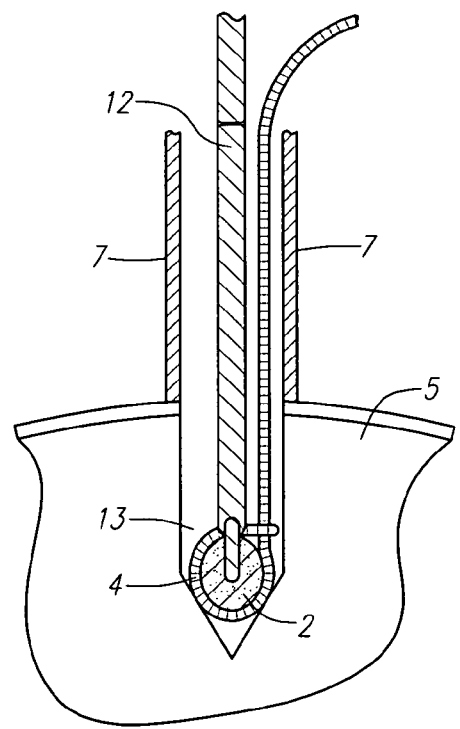
FIG. 1E                FIG. 1F

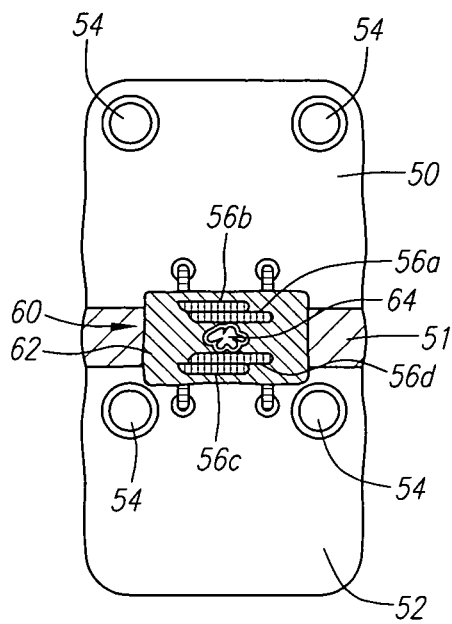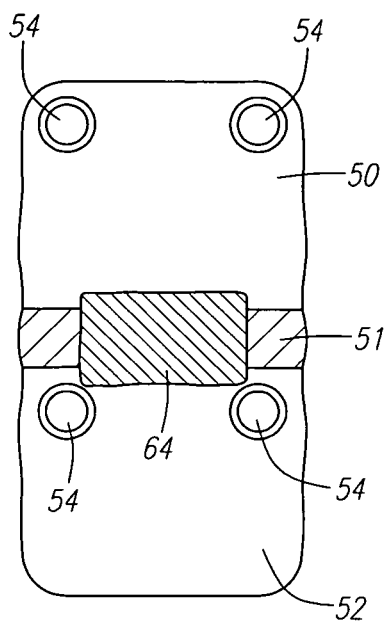
FIG. 5C    FIG. 5D
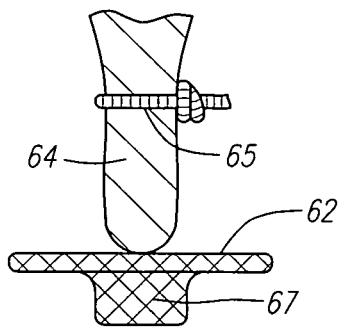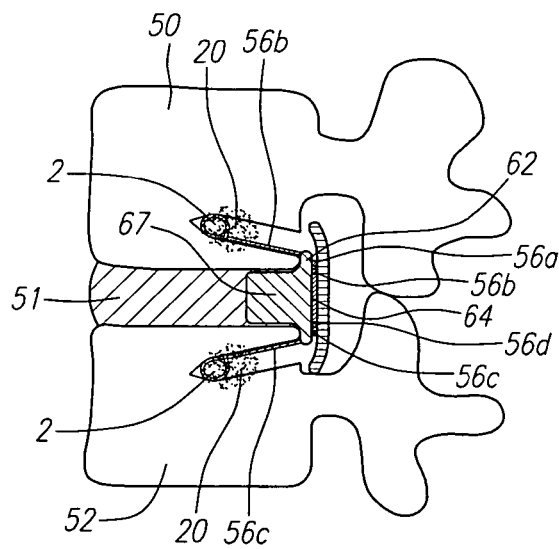
FIG. 5E    FIG. 5F
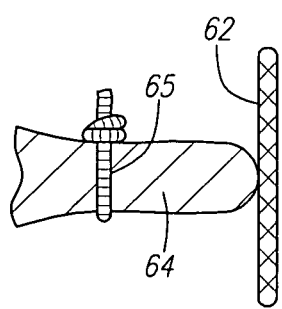
FIG. 5G

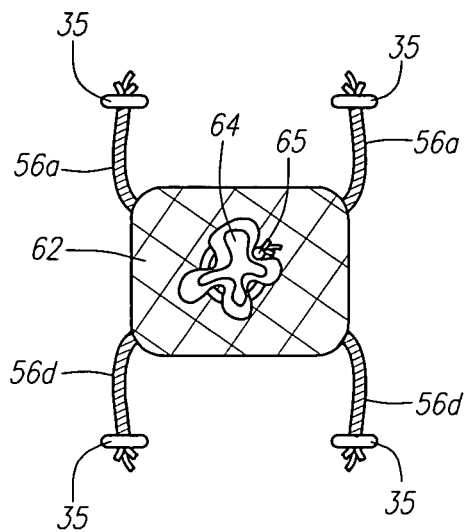
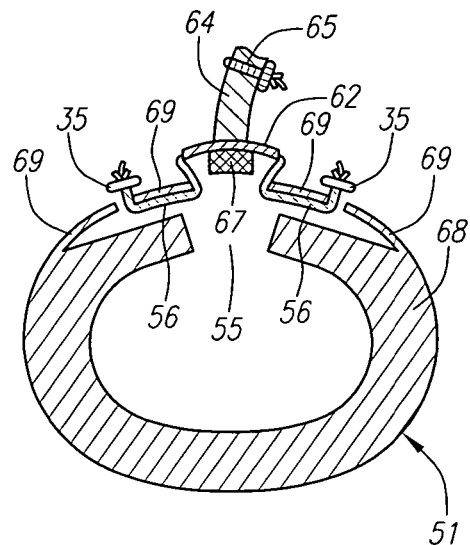
FIG. 6A
FIG. 6B
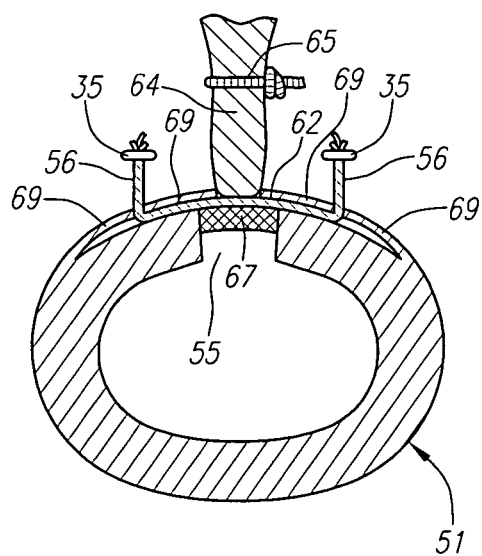
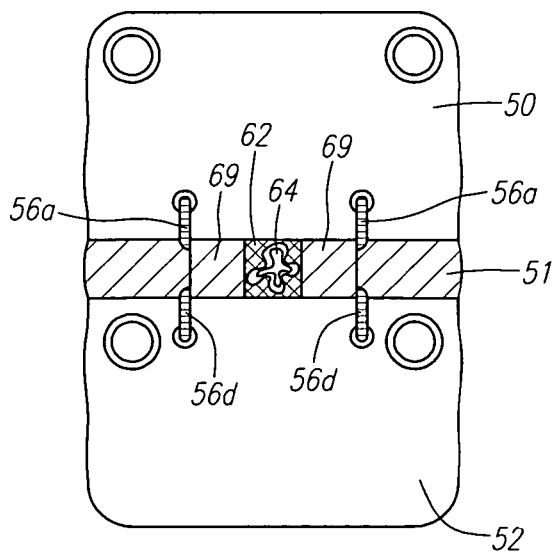
FIG. 6C
FIG. 6D

SUTURES FOR USE IN THE REPAIR OF DEFECTS IN THE ANULUS FIBROSUS

RELATED APPLICATIONS

This application claims the benefit of U.S. Provisional Patent Application 60/748,518, filed Dec. 8, 2005, the entirety of which is hereby expressly incorporated by reference herein in its entirety.

BACKGROUND OF THE INVENTION

The human intervertebral disc is an oval to kidney bean-shaped structure of variable size depending on the location in the spine. The outer portion of the disc is known as the anulus fibrosus (AF). The anulus fibrosus is formed of approximately 10 to 60 fibrous bands or layers. The fibers in the bands alternate their direction of orientation by about 30 degrees between each band. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. A high water content (approximately 70-80%) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50% of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85% at birth to approximately 70% in the elderly. The ratio of chondroitin sulfate to keratin sulfate decreases with age, while the ratio of chondroitin 6 sulfate to chondroitin 4 sulfate increases with age. The distinction between the annulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. This disc pathology can result in: 1) bulging of the annulus into the spinal cord or nerves; 2) narrowing of the space between the vertebra where the nerves exit; 3) tears of the annulus as abnormal loads are transmitted to the annulus and the annulus is subjected to excessive motion between vertebra; and 4) disc herniation or extrusion of the nucleus through complete annular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either remove the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the annulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in co-pending U.S. patent application Ser. No. 10/407,554 and U.S. Pat. No. 6,878,167, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often allies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

Suture anchors are commonly used in surgery on the shoulder, knee, and other joints about the body. The devices fasten one end of the suture to the bones that form the joint. The second end of the suture is passed through soft tissues such as the rotator cuff of the shoulder. The sutures are used to attach the soft tissues to the bones that form the joints. Prior-art suture anchors can be pulled from the bone if too much tension is applied to the suture.

SUMMARY OF THE INVENTION

The present invention offers surgeons a suture anchor with improved resistance to pullout. In-situ curing cement such as Polymethylmethacrylate (PMMA) or a bioactive cement such as MIG3 (Wright medical) are injected into the bone surrounding the first end of the suture. The cement is injected after placement of the first end of the suture into the bone. The cement acts as grout to trap the suture in holes in the bones. An anchor or other enlargement at the end of the suture can become entrapped behind the cement that cures in situ. The cement does not necessarily act as an adhesive. The in-situ curing material is forced behind pieces of bone, generally cancellous bone.

In one embodiment, a method for anchoring a suture to a bone is provided. A hole is first formed in a bone. A suture having a first and second end is coupled to an anchor in the shape of a spool or a ring, wherein the first end is coupled to the anchor. The anchor and coupled suture are then placed into the hole such that the second end of the suture remains externally available. A curing material is then injected into the hole. The second end of the suture could then be attached to a device or to a second suture that is also anchored to the bone. In one embodiment, the hole could be made in a vertebra of a patient adjacent to a vertebral disc with a defect.

In another embodiment, a device for fixing a defect in the anulus fibrosus includes a mesh patch having at least a first and second layer. The device also includes first and second sutures, each having a first end, a middle portion, and a second end, wherein the middle portion of the first and second sutures are positioned between the first and second layers. Additionally, there are first, second, third, and fourth anchors associated with the first and second ends of the first and second sutures, respectively.

In use, the device can be positioned such that the mesh device is adjacent the defect in the vertebral disc. First and second holes can be formed in a vertebra cranial to the vertebral disc and first and second holes can also be formed in the vertebra caudal to the vertebral disc. The first and second ends of the first suture are then inserted into the first and second holes in the vertebra cranial to the vertebral disc and the first and second ends of the second suture are inserted into the first and second holes in the vertebra caudal to the vertebral disc. A curing material is then injected into the first and second holes in the vertebrae cranial and caudal to the vertebral disc such that the first and second ends of the first and second sutures are surrounded by the curing material.

In another method, a defect in a vertebral disc of a patient is treated by providing first, second, third, and fourth sutures, each having a first end and a second end. First and second holes are formed in a vertebra cranial to the vertebral disc and first and second holes are also formed in the vertebra caudal to the vertebral disc. The first ends of the first and second sutures are then inserted into the first and second holes in the vertebra cranial to the vertebral disc. The first ends of the third and fourth sutures are also inserted into the first and second holes in the vertebra caudal to the vertebral disc. A curing material is then injected into the first and second holes in the vertebrae cranial and caudal to the vertebral disc such that the first ends to the first, second, third, and fourth sutures are surrounded by the curing material. The first, second, third, and fourth sutures are then attached to a mesh device. The mesh device may be attached by passing the second ends of the first, second, third, and fourth sutures through first, second, third, and fourth locations on the mesh device, respectively. The mesh device is then positioned adjacent the defect, which may either be on top of or below the posterior longitudinal ligament. Each of the second ends of the first, second, third, and fourth sutures are then attached to at least one of the second ends of the first, second, third, and fourth sutures. In one embodiment of this invention, a distance between the first and second holes in the vertebra cranial to the vertebral disc is larger than a distance between the first and second locations in the mesh device. Similarly, a distance between the first and second holes in the vertebra caudal to the vertebral disc is larger than a distance between the third and fourth locations in the mesh device. Furthermore, portions of the mesh device could extend to cover a portion of the vertebrae between the pairs of holes in the cranial and caudal vertebrae. That is, portions of the mesh device that lie between the pairs of holes in the cranial and the caudal vertebrae can be smaller than the distance between the pairs of holes in the cranial and the caudal vertebrae. Such configuration requires the use of flexible fixation components (sutures) that are anchored to the vertebrae and extend through or over the mesh. Passing such sutures through the mesh enables the sutures to apply tension to the mesh device as the sutures are tightened. Alternatively, the mesh device may have dimensions that are larger than the distance between the pairs of holes in the cranial and the caudal vertebrae.

In another method, a defect in a vertebral disc of a patient is treated by providing first, second, third, and fourth sutures. The first and second sutures are fastened to a vertebra cranial to the vertebral disc at first and second locations, respectively. The third and fourth sutures are fastened to a vertebra caudal to the vertebral disc at third and fourth locations, respectively. A mesh device having a first and second side is positioned such that the first side is adjacent the defect. The first, second, third, and fourth sutures are positioned against the second side of the mesh device. Tension is then applied to the first, second, third, and fourth sutures. Each of the first, second, third, and fourth sutures is then attached to at least one of the first, second, third, and fourth sutures, thereby holding the mesh device adjacent the defect.

In another method, a defect in a vertebral disc of a patient is treated by providing first, second, third, and fourth sutures. The first and second sutures are fastened to a vertebra cranial to the vertebral disc at first and second locations, respectively. The third and fourth sutures are fastened to a vertebra caudal to the vertebral disc at third and fourth locations, respectively. A device is then positioned adjacent the defect. The first, second, third, and fourth sutures are positioned against the device. Tension is then applied to the first, second, third, and fourth sutures. Each of the first, second, third, and fourth sutures is then welded to at least one of the first, second, third, and fourth sutures, thereby holding the device adjacent the defect.

In another embodiment, the invention includes a device for fixing a defect in the anulus fibrosus or vertebral disc of a patient. The device includes a mesh patch and an anti-adhesion component attached to a portion of the mesh patch in a contracted configuration, where the anti-adhesion component is capable of being opened into an expanded configuration. The device also includes a constraining element holding the anti-adhesion component in the contracted configuration. The anti-adhesion component may be attached to a center portion of the mesh patch or at least one edge of the mesh patch. In the contracted configuration, the anti-adhesion cover may be bunched together, rolled, or gathered. The constraining element may be a band or suture that is tied around the anti-adhesion component. In one embodiment, the mesh patch may also include a mesh plug adapted to substantially fill the defect, wherein the mesh plug is located on a side of the mesh patch opposite the attached anti-adhesion component, With respect to the above methods, the mesh devices and sutures may be placed above (i.e., on top of) or below (i.e., underneath) the posterior and/or anterior longitudinal ligament that overlays the vertebral disc and surrounding vertebrae. Depending on the location of the defect in the disc, the invention may be used over the posterior, anterior, or lateral portions of the cervical, thoracic, or lumbar spine. Therefore, in one embodiment, the first, second, third, and fourth sutures may be passed beneath the posterior or anterior longitudinal ligament such that at least a portion of the first, second, third, and fourth sutures are covered by a portion of the posterior or anterior longitudinal ligament after the mesh device is placed adjacent the defect. In this embodiment, the mesh device may be either above or below the posterior or anterior longitudinal ligament. Where the mesh device is placed beneath the posterior or anterior longitudinal ligament, the posterior or anterior longitudinal ligament could act as a barrier to prevent the formation of adhesions on the posterior or anterior (outwardly facing) side of the mesh device. Where the mesh device is on top of the posterior or anterior longitudinal ligament, an anti-adhesion cover may be expanded over the mesh device to prevent adhesions from forming. Additionally, where the mesh device is placed over the posterior or anterior longitudinal ligament, the portion of the posterior or anterior longitudinal ligament adjacent or near the mesh device could be intentionally injured to stimulate the posterior or anterior longitudinal ligament to heal. Cells from the posterior or anterior longitudinal ligament could migrate from the posterior or anterior longitudinal ligament to the mesh device as it heals. The posterior longitudinal ligament, anterior longitudinal ligament, and/or the anulus fibrosus could be injured by abrading, scraping, or cutting.

In the above methods and devices, the first, second, third, and fourth sutures may be fastened or otherwise coupled or attached to the vertebrae at first, second, third, and fourth locations, respectively. The sutures can be attached or fastened to the surrounding vertebrae using a variety of methods, which include suture anchors and curing materials. The suture anchors may be variations of bone screws, having eyelets or hooks adapted to receive sutures therethrough. Alternatively, the sutures may be attached or fastened by inserted the sutures into holes in the vertebrae and surrounding the sutures with cement or other curing material. Additional anchors having enlarged diameters may be attached to the ends of the sutures before inserting them into the holes and inserting the bone cement. In one embodiment, the sutures can be attached using different methods. For example, one or two of the sutures could be attached to a vertebra using bone cement while the other remaining sutures could be attached using suture anchors such as bone screws. The sutures can be attached to the surrounding vertebrae at locations that are to the left and the right of the defect. The first and second sutures that are fastened to the vertebra cranial to the disc are separated by a first distance. The third and fourth sutures that are fastened to the vertebra caudal to the disc are separated by a second distance. The first and third sutures that are fastened to the vertebrae are separated by a third distance. And the second and fourth sutures that are fastened to the vertebrae are separated by a fourth distance.

In the above methods and devices, the mesh device or patch, having a length and a width, can be sized such that the width is smaller than the third and fourth distances, i.e., the mesh device is smaller than the distance between the attachment of generally vertically aligned sutures attached to the surrounding vertebrae. Alternatively, the mesh device can be sized such that the width is larger than the third and fourth distances, i.e., the mesh device is larger than the distance between the attachment of generally vertically aligned sutures attached to the surrounding vertebrae. Similarly, the mesh device may be sized such that the length of the device is smaller than first and second distances, i.e., the mesh device is smaller or shorter than the distance between the attachment of generally horizontally aligned sutures attached to the same vertebra. Alternatively, the mesh device may be sized such that the length of the device is larger than first and second distances, i.e., the mesh device is larger or longer than the distance between the attachment of generally horizontally aligned sutures attached to the same vertebra. The mesh device or patch may also include a mesh plug adapted to substantially fill the defect. Where an anti-adhesion cover is present, this mesh plug would be located on the opposite side of the mesh patch or device than the anti-adhesion cover.

In the above methods and devices, tension can be applied to the sutures. The tension can be applied in various directions. For example, tension can be applied in a left to right direction, i.e., first apply tension to the sutures attached to the right of the defect and then apply tension to the sutures attached to the left of the defect. Similarly, tension can be applied from a head to foot direction, i.e., first apply tension to the sutures attached to the vertebra cranial of the defect and then apply tension to the sutures attached to the vertebra caudal of the defect. Alternatively, tension could be applied in a right to left, foot to head, right diagonal to left diagonal, or left diagonal to right diagonal direction.

In the above methods and devices, the sutures may be attached by welding. Each of the first, second, third, and fourth sutures may be welded to at least one of the first, second, third, and fourth sutures. The sutures may be welded in a pattern having diagonal connections, generally upper and lower horizontal connections, and/or generally left and right vertically extending connections. For example, the first suture could be welded to the second suture and the third suture could be welded to the fourth suture. Alternatively, the first suture could be welded to the third suture and the second suture could be welded to the fourth suture. Alternatively, the first suture could be welded to the fourth suture and the second suture could be welded to the third suture. Any other variation of attachment is also possible, including a combination or vertical, diagonal, and/or horizontal connections in the same device or method.

In the above methods and devices, an anti-adhesion component may additionally be expanded to cover the mesh device. The anti-adhesion cover may be attached to a portion of the mesh device and could be made from wherein ePTFE, Sepratfilm, allograft, or absorbable materials. The absorbable materials may include oxidized atelocollagen type I, polyethylene glycol, glycerol, and combinations thereof. The anti-adhesion cover may be attached to a portion of the mesh patch or device in a contracted configuration, where the anti-adhesion component is capable of being opened into an expanded configuration. The anti-adhesion component may be attached to a center portion of the mesh patch or at least one edge of the mesh patch. In the contracted configuration, the anti-adhesion cover may be bunched together, rolled, or gathered. The anti-adhesion component may be held in the contracted configuration by a constraining element. The constraining element may be a band or suture that is tied around the anti-adhesion component.

Additionally, in the above methods and devices, anchors having enlarged diameters or cross-sections may be attached to the ends of the sutures that are inserted into holes in the surrounding vertebrae. These anchors serve to enlarge the free ends of the sutures and help to strengthen the attachment of the sutures to the bone. The anchors may be in the form of a ring having a hole for a suture to be disposed therethrough or a spool having an indentation adapted to fit a suture. The anchor may also have a first portion having a pointed tip and a second portion having an attachment means, such as an eyelet or hook, to couple to the suture.

The invention can be used to facilitate healing of the anulus fibrosus, facilitate healing of the anterior longitudinal ligament, facilitate healing of the posterior longitudinal ligament, contain the nucleus pulposus, contain bone growth material such as allograft, autograft, Bone Morphogenetic Protein (In-Fuse, Medtronic Sofamor Danek, Memphis, Tenn.) or other bone growth material, contain intradiscal cages, contain nucleus replacement (NR) devices, and to contain total disc replacement (TDR) devices. The invention may also be used to restrict spinal motion. The invention may severely restrict motion to facilitate spinal fusion or restrict excessive motion that may occur with TDR devices.

BRIEF DESCRIPTION OF THE FIGURES

FIG. 1A illustrates an anterior view of a spool.

FIG. 1B illustrates a lateral view of the spool of FIG. 1A.

FIG. 1C illustrates a lateral view of the spool of FIG. 1A with a suture.

FIG. 1D illustrates a lateral view of the spool of FIG. 1A with a suture tightened about the spool.

FIG. 1E illustrates a sagittal cross-section or a portion of a bone, drill sleeve, and a drill bit.

FIG. 1F illustrates a sagittal cross-section of a portion of a bone, drill sleeve, a drill bit, and the invention of FIG. 1D.

FIG. 5C illustrates a posterior view of a coronal cross section through a segment of the spine and the embodiment of the invention drawn in FIG. 5B, with the free ends of the sutures welded or otherwise fastened to each other or the mesh device.

FIG. 5D illustrates a posterior view of a coronal cross section through a segment of the spine and the embodiment of the invention drawn in FIG. 5B, with an anti-adhesion component expanded to cover the mesh device.

FIG. 5E illustrates a lateral view of an alternative embodiment of the invention with an anti-adhesion cover and a projection adapted to extend into a defect.

FIG. 5F illustrates a lateral view the sagittal cross section of a segment of spine with the invention of FIG. 5E inserted into and covering the defect.

FIG. 5G illustrates a lateral view of an alternative embodiment of the invention with an anti-adhesion component or cover.

FIG. 6A illustrates a posterior view of an alternative embodiment of the invention that includes sutures with enlarged ends that course through the mesh device.

FIG. 6B illustrates an exploded view of an axial cross section through a disc with the invention drawn in FIG. 6A.

FIG. 6C illustrates a cranial view of an axial cross section through a disc with the invention drawn in FIG. 6B.

FIG. 6D posterior view of a coronal cross section through a segment of the spine and the embodiment of the invention drawn in FIG. 6C.

DETAILED DESCRIPTION OF THE INTENTION

Figure 1G:
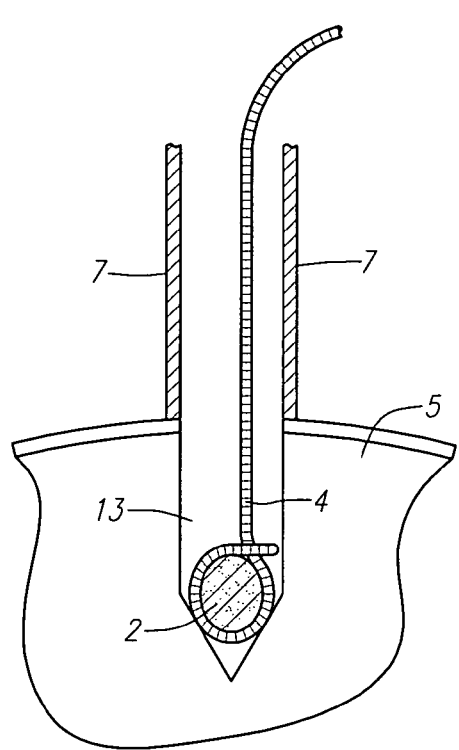
FIG. 1G illustrates a sagittal cross-section of a portion of a bone and the invention of FIG. 1F.

FIG. 1A is an anterior view of one embodiment of the invention. Device 2 is a spool having indentation 3 adapted for placement of a suture around the spool such that the suture fits at least partially within the indentation. Indentation 3 aids in keeping the suture looped around spool 2. Device 2 may be made of metal such as Titanium, plastic such as polyethylene or PEEK, bioresorbable materials, or cured cement such as PMMA. Suitable bio-resorbable materials include polylactic acid (PLA), polyglycolic acid (PGA), poly (ortho esters), poly(glycolide-co-trimethylene carbonate), poly-L-lactide-co-6-caprolactone, polyanhydrides, poly-n-dioxanone, and poly(PHB-hydroxyvaleric acid), FIG. 1B is a lateral view of spool 2. FIG. 1C is a lateral view of spool 2 and suture 4 looped around spool 2. FIG. 1D is a lateral view of the embodiment of the invention drawn in FIG. 1C. Suture 4 has been tightened around spool 2.

FIG. 1E is a sagittal cross section of a portion of bone 5, drill sleeve 7, and drill bit 9. Drill bit 9 has stop feature 10 that cooperates with sleeve 7 to limit the depth that drill bit 9 is inserted into bone 5.

FIG. 1F is a sagittal cross section of a portion of bone 5, drill sleeve 7, and the embodiment of the invention drawn in FIG. 1D. Grasping tool 12 is used to place the first end of suture 4 and spool 2 into hole 13 in bone 5. Suture 4 and spool 2 may be press-fit into bone 5. Alternatively, the loop of suture can be placed into the hole without the spool (not shown).

FIG. 1G is a sagittal cross section of a portion of bone 5 and the embodiment of the invention drawn in FIG. 1F. Suture 4 and spool 2 have been placed into hole 13 in bone 5.

Figure 1H:
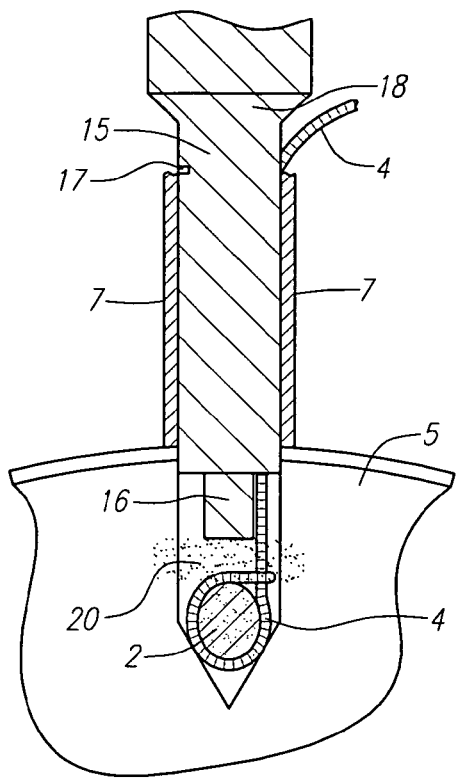
FIG. 1H illustrates a sagittal cross-section of a portion of a bone, the embodiment depicted in FIG. 1G, and a cement injection tool.

FIG. 1H is a sagittal cross section of bone 5, the embodiment of the invention drawn in FIG. 1G and cement injection tool 15. A plunger instrument may be used to fully seat the suture and spool before insertion of the cement injection tool. Tip 16 of the cement-injecting tool 15 may have marking 17 that may be used with sleeve 7 to assure tip 16 of cement-injecting tool 15 is inserted to the proper depth into hole 13. Alternatively, tip 16 of the injection tool may have depth stop feature 18 that cooperates with sleeve 7 to ensure that tip 16 is inserted into the proper depth. Tip 16 of the cement-injecting tool preferably has an elastic or deformable sleeve to help seal the hole in the bone. Extrusion of cement 20 from the hole can also be minimized by press fitting the cement-injecting tool tip into the hole, limiting the amount of cement in the syringe, allowing the in-situ curing cement to partially cure before injecting the cement, and injecting a small amount of air or fluid from the tip of the instrument before injecting the cement.

Figure 1I:
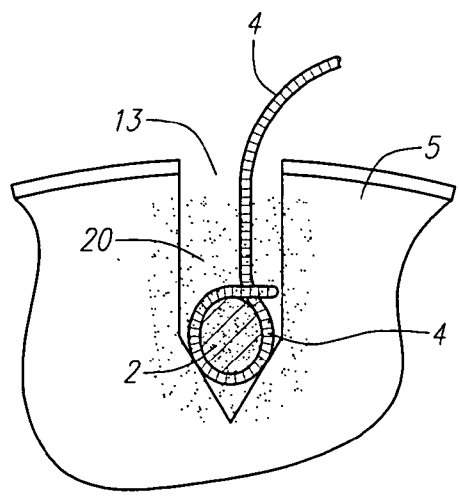
FIG. 1I illustrates a lateral view of a sagittal cross-section of a portion of a bone and the embodiment of the invention depicted in FIG. 1D.

FIG. 1I is a lateral view of a sagittal cross section a portion of bone 5 and the embodiment of the invention drawn in FIG. 1D. In-situ curing cement has been injected into hole 13 and around spool 2 with associated suture 4. Cement 20 interdigitates with bone 5 surrounding hole 13 to fasten spool 2 and suture 4 to bone 5. Cement 20 preferably acts more as a grout than as an adhesive.

Figure 1J:
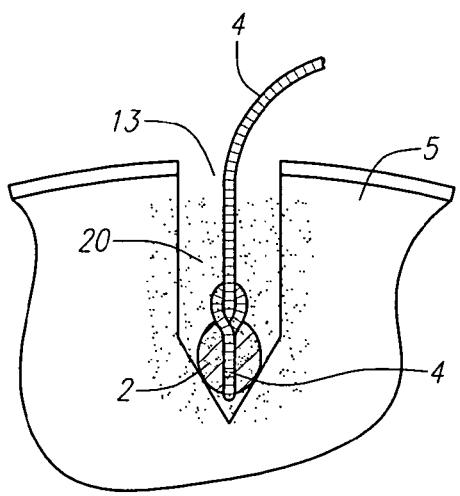
FIG. 1J illustrates an anterior view of a coronal cross-section of a portion of a bone and the embodiment depicted in FIG. 1I.

FIG. 1J is an anterior view of a coronal cross section of a portion of bone 5 and the embodiment of the invention drawn in FIG. 1I.

Figure 2A:
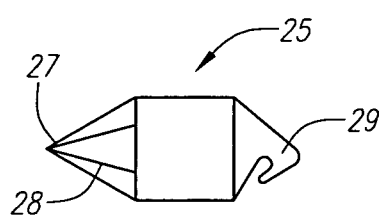
FIG. 2A illustrates a lateral view of an alternative embodiment of the invention having a pointed tip.

FIG. 2A is a lateral view of an alternative embodiment of the invention. Device 25 has pointed tip 27. Facets ridges, or cutting flutes 28 extend from pointed tip 27. The opposite end of device 25 has a feature such as hook 29 that may be used to retain a suture. Device 25 can be made of metal such as titanium, ceramic, bio-resorbable material, or plastic such as PEEK.

Figure 2B:
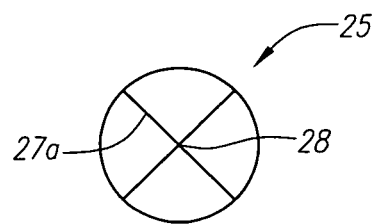
FIG. 2B illustrates an alternative view of the embodiment of the invention of FIG. 2A.

FIG. 2B is a view of pointed end 27 with ridges 28 of the embodiment of the invention drawn in FIG. 2A. Pointed end 27a of device 25 is shown with a circular cross-section.

Figure 2C:
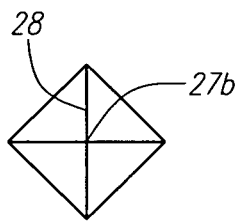
FIG. 2C illustrates an alternative embodiment of FIG. 2A.

FIG. 2C is a view of the pointed end of an alternative embodiment of the invention drawn in FIG. 2A. Pointed tip 27b of the device has a square cross-section than the device drawn in FIG. 2B.

Figure 2D:
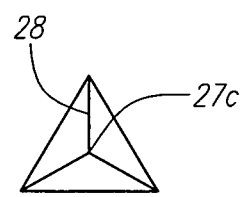
FIG. 2D illustrates another alternative embodiment of FIG. 2A.

FIG. 2D is a view of the pointed end of an alternative embodiment of the invention drawn in FIG. 2A. Pointed tip 27c of the device has a triangular shape. Devices with alternative shapes or cross-sections such as pentagons, hexagons, heptagons, octagons, or other polygonal shapes may be used in the invention.

Figure 2E:
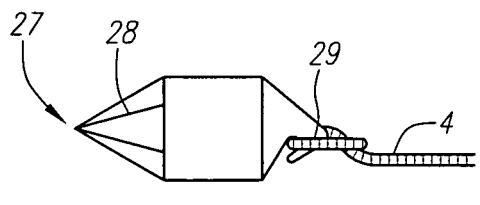
FIG. 2E illustrates a lateral view of the embodiment of the invention depicted in FIG. 2A.

FIG. 2E is a lateral view of the embodiment of the invention drawn in FIG. 2A and suture 4. Suture 4 has been looped through attachment feature 29 on the pointed device 25.

Figure 2F:
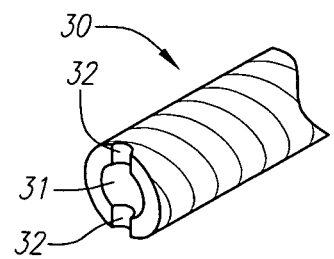
FIG. 2F illustrates an oblique view of an insertion tool.

FIG. 2F is an oblique view of the end of tool 30 that can be used to insert the pointed tip device and the suture. Tool 30 has an open proximal end, an open distal end, and a lumen therebetween. The suture can be passed through the lumen and out of the open distal end of the tool. Slots 32 on the sides of the tip of tool 30 are configured to straddle hook feature 29 on pointed tip device 25.

Figure 2G:
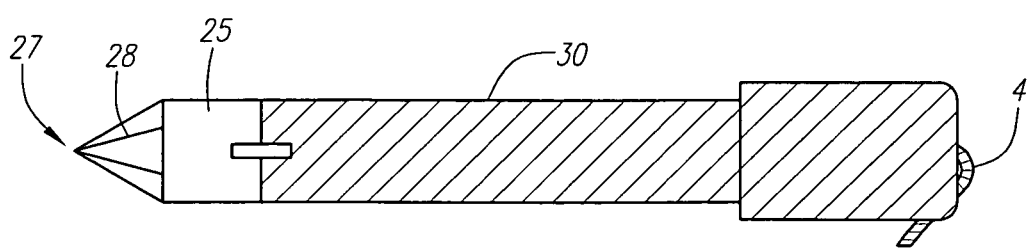
FIG. 2G illustrates a lateral view of the embodiment of the invention drawn in FIGS. 2E and 2F.

FIG. 2G is a lateral view of the embodiment of the invention drawn in FIGS. 2E and 2F. Suture 4 has been passed through the lumen of insertion tool 30 and attached to the handle of the tool. Tension on suture 4 holds the pointed tip device 25 onto insertion tool 30. Insertion tool 30 may be impacted and twisted back and forth to insert pointed tip device 25 into bone.

Figure 2H:
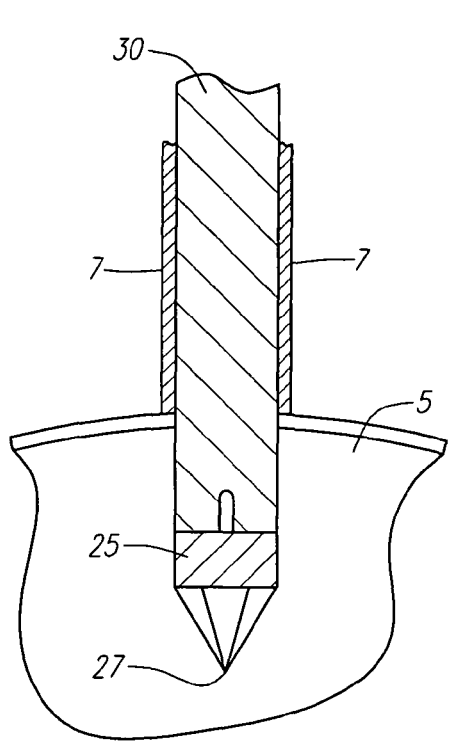
FIG. 2H illustrates a sagittal cross-section of a portion of a bone and the embodiment of the invention drawn in FIG. 2G.

FIG. 2H is a sagittal cross section of a portion of bone 5 and the embodiments of the invention drawn in FIG. 2G. Pointed tip device 25 has been inserted into bone 5 through drill sleeve 7.

Figure 2I:
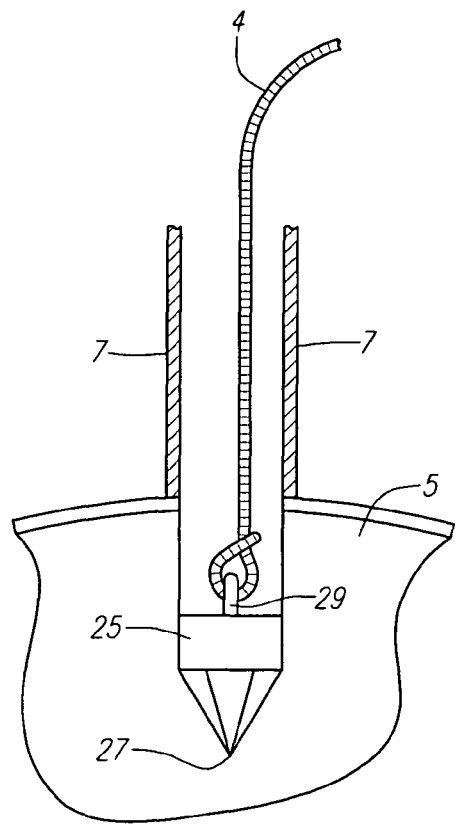
FIG. 2I illustrates a sagittal cross-section of a portion of a bone and the embodiment of the invention drawn in FIG. 2E.

FIG. 2I is a sagittal cross section of a portion of bone 5 and the embodiment of the invention drawn in FIG. 2E. Pointed tip device 25 has been inserted into bone 5. Tension on suture 4 helps hold suture 4 on hook feature 29 of pointed tip device 25.

Figure 2J:
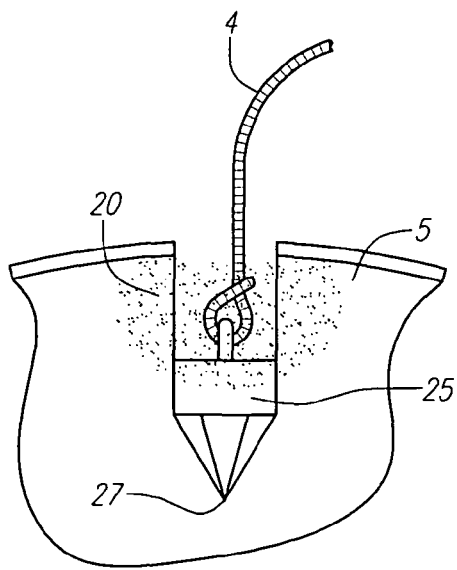
FIG. 2J illustrates a sagittal cross-section of a portion of a bone and the embodiment of the invention drawn in FIG. 2I.

FIG. 2J is a sagittal cross section of a portion of bone 5 and the embodiment of the invention drawn in FIG. 2I. In-situ curing cement 20 has been injected over pointed tip device 25. A tool similar to the tool drawn in FIG. 1H may be used to inject the cement. Cured cement 20 blocks pointed tip device 25 from extruding from bone 5 when tension is applied to device 25. Pointed tip device 25 can be pulled out with minimal force before cement 20 is injected on top of device 25.

Figure 3:
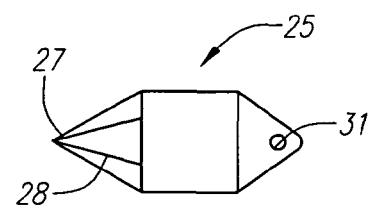
FIG. 3 illustrates a lateral view of an alternative embodiment of an invention having a pointed tip.

FIG. 3 is a lateral view of an alternative embodiment of the invention drawn in FIG. 2A. Pointed tip device 25 has an eyelet 31. A suture may be passed through the eyelet.

Figure 4A:
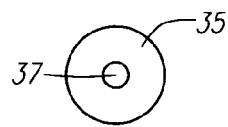
FIG. 4A illustrates an alternative embodiment of an anchor shaped like a ring.
Figure 4B:
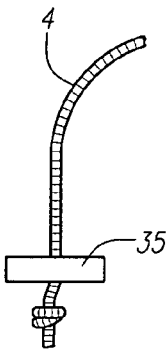
FIG. 4B illustrates a lateral view of the embodiment of FIG. 4A with a suture passing through the ring-like device.

FIG. 4A illustrates an alternative anchor shaped like a ring having a circular portion 35 surrounding hole 37. FIG. 4B is a lateral view of the tip of the embodiment of the invention drawn in FIG. 4A. Suture 4 has been passed through the hole of ring-like device 35. Suture 4 has been knotted or otherwise enlarged to prevent the first end of the suture from being pulled through the opening in ring 35. Ring 35 could be made of metal, plastic, cured cement, or other material. The ring preferably has elastic properties.

Figure 4C:
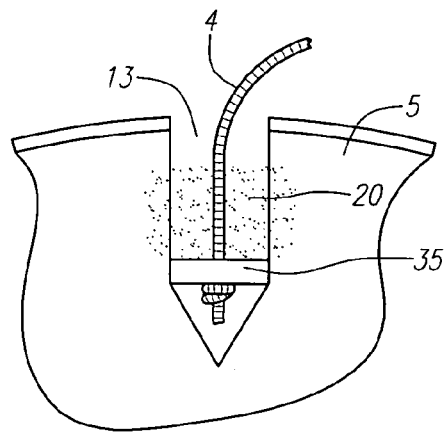
FIG. 4C illustrates a sagittal cross section of the invention of FIG. 4B inserted into a portion of a bone.

FIG. 4C is a sagittal cross section through a portion of bone S and the embodiment of the invention drawn in FIG. 4A. Cement 20 has been injected into hole 13 after inserting device 35. Cement 20 was injected under sufficient pressure to force cement 20 into bone 5 surrounding hole 13. Alternatively, the knotted end of suture 4 can be cemented into hole 13 in the vertebra without ring component 35.

Figure 5A:
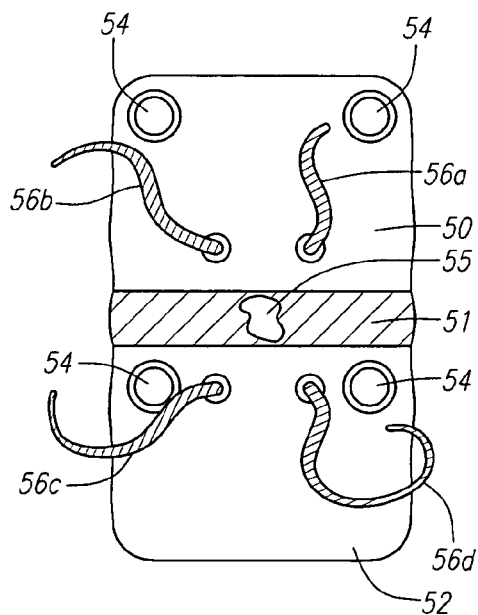
FIG. 5A illustrates a posterior view of a coronal cross section through a segment of the spine with sutures fastened to the vertebrae.

FIG. 5A is a posterior view of a coronal cross section through a segment of the spine with transected pedicles 54 and having an aperture or defect 55 in disc 51. Two sutures 56a and 56b have been fastened to vertebra 50 above disc 51 and two sutures 56c and 56d have been fastened to vertebra 52 below disc 11. The sutures are preferably made of nylon, polyester, or other weld-able material. Alternatively, the sutures could be made of resorbable material such as PDS (Ethicon, Somerville, N.J.). The sutures are preferably size #2 (0.5 mm). Alternatively, 5-0 to #5 sized suture could be used. Sutures 56a-d have been fastened to cranial and caudal vertebrae 50, 52 using any of the implant and anchor devices previously described. Other types of suture anchors may also be used to fasten sutures to the vertebrae. These alternative suture anchors are described in U.S. Application Ser. Nos. 60/861,499, filed Nov. 28, 2006, and 60/808,795, filed May 30, 2006, all of which are hereby expressly incorporated by reference in their entirety for all purposes. Suitable suture anchors may also be used to fasten sutures to the vertebrae. The suture anchors are preferably 3 mm, 4 mm, 5 mm, or 6.5 mm in diameter and 5 mm, 6 mm, 7 mm, 10 mm, or 15 mm in length. Alternatively, the suture anchors could be larger than 6.5 mm in length and longer than 10 mm in length. The suture anchors are preferably made of MRI compatible material such as titanium, plastic, or bio-resorbable material. The anchors are preferably recessed within the vertebrae. Such placement allows bone to grow into the holes in the vertebrae and across the proximal ends of the anchors. The configuration allows bone to completely encapsulate the anchors and help prevent extrusion of the anchors. In one embodiment, at least one of the sutures may be fastened to a vertebra using a curing material while another suture may be fastened to a vertebra through a suture anchor that is screwed into the vertebra. In one embodiment, the two sutures in a single vertebra may be positioned at a distance greater than the distance between where the second ends of the sutures attach to the mesh device. Such a configuration enables the fixation components, i.e., the sutures and anchors, to apply tension to the mesh device. Tension on the mesh component increases the stiffness of the mesh component. Thus, this configuration allows the thin, flexible material of the mesh component to resist the pressure from the nucleus pulposus, thereby preventing bulging of the mesh component as nucleus pulposus and other materials accumulate under and apply pressure to the mesh.

Figure 5B:
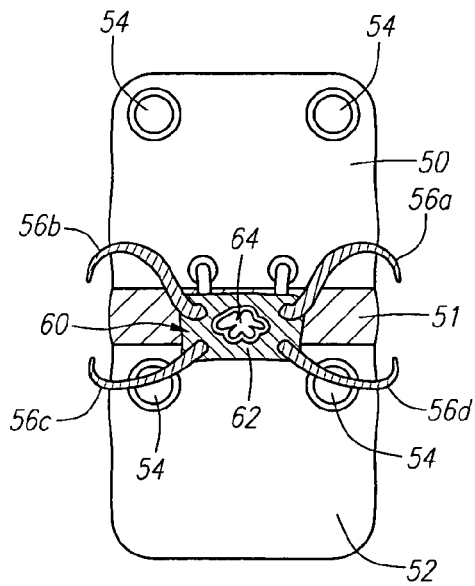
FIG. 5B illustrates a posterior view of a coronal cross section through a segment of the spine and the embodiment of the invention drawn in FIG. 5A, with the free ends of the sutures passing through an annular repair device.

FIG. 5B is a posterior view of a coronal cross section through a segment of the spine and the embodiment of the invention drawn in FIG. 5A. The free ends of sutures 56a-d were passed through annular repair device 60 having mesh component or patch 62 and anti-adhesion cover 64. Instruments could be used to measure the distance between the holes in the spine. Such measurements would help surgeons pass the sutures through optimal locations in the mesh device. Device 60 is configured to maximize tissue in-growth. For example, mesh component 62 could be made of polyester, polypropylene, expanded polytetrafluoroethylene (ePTFE), allograft, or xenograft. The interstitial pore sizes of the mesh are preferably larger than three microns. The interstitial pore size of the mesh is preferably larger than 150 microns to maximize tissue in-growth from the disc. The mesh, made of material configured for tissue in-growth, preferably has a burst strength of between 100 and 350 PSI. Similarly, the sutures and the method used to fasten the sutures, should preferably have sufficient tensile strength to hold the mesh device against the disc with pressures on the device as high as 350 psi. The sutures are preferably passed through reinforced sections of mesh. The mesh may be reinforced as described in co-pending application 60/808,795, which was previously incorporated by reference. Additionally, the peripheral 2 to 3 mm of the mesh could be reinforced with material that is sewn into and over the mesh. For example, #2 sized multi-filament polyester suture such Orthocord (DePuy, Raynham, Mass.) or Fiberwire (Arthrex, Naples, Fla.) or other materials with other diameters could be used to reinforce the tensile strength of the periphery of the mesh. Sutures 56a-d are preferably passed through the mesh on the central side of the reinforced area. Tension on sutures passed in such location tightens the mesh and pull against the reinforced are of the mesh. Alternatively, the sutures could pass through reinforced eyelets in the mesh. The eyelets are preferably connected to one another with strands of high-tensile strength polyester. Alternatively, the mesh device could be manufactured with the sutures incorporated in the mesh. Impacted or radially expanding anchors could be used in such embodiment of the invention. Threaded anchors are preferably used when sutures are fastened to the spine before fastening the mesh to the spine.

Anti-adhesion component 64 is seen folded on the posterior surface of mesh component 62. A suture has been looped around anti-adhesion component 64 to hold it in its contracted shape. Anti-adhesion component 64 is also attached to a portion of the in-growth mesh component 62. Anti-adhesion component 64 is only attached to a portion of the mesh component, rather than laminating the mesh and anti-adhesion components or attaching the two components along their edges. Such a configuration enables fluids to pass between the porous mesh and the anti-adhesion component, thereby preventing the accumulation of fluids beneath the anti-adhesion component. In one embodiment, the anti-adhesion component may be attached at only the center portions of the mesh and anti-adhesion components. The anti-adhesion component may have a first, collapsed configuration that facilitates insertion of the device by avoiding obstruction of the surgeon's view of the device. The anti-adhesion component may also have a second, expanded configuration that covers the porous mesh component, and possibly the fixation members and the holes in which the fixation members are inserted into the spine. Alternatively, the anti-adhesion component could be fastened to the mesh or the sutures or both, after welding the sutures. For example the anti-adhesion component could be fastened to the mesh or sutures with an additional suture. The ends of the additional suture could be welded together to fasten the anti-adhesion component to the other components of the device. Alternatively, the anti-adhesion component could be glued to the mesh or otherwise fastened in-situ. For example, a biocompatible glue, such as a Cyanoacrylate, could be used to fasten the components. Anti-adhesion component 64 could be made of ePTFE, Sepratfilm, allograft, or absorbable materials (such as oxidized atelocollagen type I, polyethylene glycol, and glycerol, or combinations of absorbable materials). Anti-adhesion component 64 preferably has interstitial pore sizes of 3 microns or less to discourage tissue in-growth.

FIG. 5C is a posterior view of a coronal cross section of a segment of the spine and the embodiment of the invention drawn in FIG. 5B. Sutures 56a-b connected to the vertebra 50 caudal to disc 51 have also been welded or otherwise fastened to each other or to mesh component 62. The sutures could be tied together, clamped together, or welded together with an ultrasound tool such as supplied by Axya medical (Beverly, Mass.). Welded sutures have many advantages compared to traditional suture tying techniques. First, welding the sutures together is easier and quicker than tying the sutures together. Second, suture welds are substantially smaller than the knots of tied sutures. Knots of tied sutures could compress the delicate nerves that lie over the knots. Third, suture welds are less susceptible to creep. Creep of traditional suture ties could loosen the attachment of a device to the spine. Fourth, the strength of suture welds is consistent while tied sutures are sometimes tied improperly. Fifth, the welding tools enable surgeons to apply more tension on the sutures before welding than surgeons can apply during traditional knot tying. The high tension enabled by the welding system allows surgeons to apply more tension to devices that are fastened to the spine and to fasten devices to the spine more securely. The ends of the sutures may be cut on either side of the weld with a cutting device and the excess suture can be removed. For example, an arthroscopic guillotine cutter may be used to trim the excess suture. Other fastening mechanisms or techniques could be used to fasten the sutures to each other. Tension is applied to the sutures before the sutures are fastened to each other. Tension on the sutures places tension on mesh component 62. Although the drawing illustrates fastening sutures from the same vertebra to each other, the sutures could be fastened in alternative configurations. For example, a suture from one vertebra could be fastened to a suture from an adjacent vertebra. For example, the sutures could be welded in the configuration illustrated in U.S. Pat. Nos. 6,248,106 & 6,423,065, which are hereby incorporated by reference in their entirety.

FIG. 5D is posterior view of a coronal cross section of a segment of the spine and the embodiment of the invention drawn in FIG. 5C. The band or suture that surrounded anti-adhesion component 64 has been removed. Anti-adhesion component 64 was expanded to cover the in-growth material of mesh component 62. Mesh component 62 and anti-adhesion component 64 are not attached to each other around the periphery of the device. This configuration enables fluids to escape from under anti-adhesion component 64 that is designed to prevent adhesions. Anti-adhesion component 64 may cover the holes in the vertebrae, partially cover the holes in the vertebrae, or fail to cover the holes in the vertebrae or mesh component 62.

FIG. 5E is a lateral view of an alternative embodiment of the invention. Anti-adhesion cover component 64 is bound by cord or suture 65. Mesh component 62 may have projection 67 adapted to extend into the defect in the anulus fibrosus (AF). Alternatively, mesh component 62 made of in-growth material may be limited to the supra annular surface of the anulus fibrosus.

FIG. 5F is a lateral view of the sagittal cross section of a segment of spine and the embodiment of the invention drawn in FIG. 5E. Anti-adhesion component 64 was drawn in its expended configuration covering mesh component 62. Mesh component 62 covers the defect in the anulus fibrosus. Device 60 is anchored to surrounding vertebrae 50, 52 with sutures 56*b, c*. As described previously, one end of sutures 56 have been looped around or otherwise associated with spool 2 and inserted into holes in the vertebrae. Cement 20 was then injected into the holes such that cement 20 interdigitates around suture 56, spool 5, and the surrounding bone. The holes in the cranial vertebra are preferably directed or angled towards the head. The holes in the caudal vertebra are preferably directed or angled towards the feet. The holes are preferably directed at an angle of about 30 to about 60 degrees, alternatively at an angle of about 20 to about 80 degrees relative to the long axis of the spine. Suture anchors used in alternative embodiments of the invention, can also be directed at such angles. Such angles increase the pull-out resistance of the anchors. The other end of the suture 56 was threaded through mesh component 62 and welded or otherwise fastened to an adjacent suture.

FIG. 5G is a lateral view of an alternative embodiment of the invention drawn in FIG. 5E. The component made of in-growth material does not have an intra-aperture feature. Anti-adhesion component 64 is bound by band or suture 65 and attached to mesh component 62. In this embodiment, mesh component 62 does not have a projection adapted for insertion into the defect in the anulus fibrosus.

FIG. 6A is a posterior view of an alternative embodiment of the invention. Sutures 56*a, d* with enlarged ends course through layers of the mesh device, rather than through pores or holes in the mesh. The mesh device could be a tube with the lumen of the tube coursing in a left to right direction. Alternatively, two or more layers of mesh could be connected along the cranial and caudal edges of the layers of mesh creating a tube-like structure. With these types of designs, the sutures could course through the lumen of the mesh tube and tube-like structures. Sutures 56*a, d* course from left to right between the layers of the mesh device, rather than passing from the distal to the proximal sides of the device through pores of holes in the mesh. Alternatively the sutures could be fastened to mesh component 62. The enlarged ends may comprise rings 35 or another suture anchor device for implantation into bone. Anti-adhesion component 64, bound by band or suture 65, is attached to a portion of mesh component 62.

FIG. 6B is a cranial view of an axial cross section through disc 51 and the embodiment of the invention drawn in FIG. 6A. The sutures have been passed between anulus fibrosus 68 and the posterior longitudinal ligament (PLL) 69 or between layers of anulus fibrosus 68. The ends of sutures 56 exit from windows cut into posterior longitudinal ligament 69 or anulus fibrosus 68. Sutures 56 are used to pull mesh component 62 between anulus fibrosus 68 and posterior longitudinal ligament 69 or between layers of the anulus fibrosus 68.

As explained above, all or only a portion of the device can be placed under the posterior longitudinal ligament. Alternatively, the mesh component can be placed over the posterior longitudinal ligament, with the sutures inserted through the posterior longitudinal ligament and into the vertebrae. An anti-adhesion cover can be placed over the mesh component and the sutures. In one method, the mesh component and anti-adhesion component can be placed over the posterior longitudinal ligament without injuring the posterior longitudinal ligament. Injury to the posterior longitudinal ligament or the anulus fibrosus increases the risk of extrusion of the nucleus pulposus. In an alternative method, the mesh component can be placed over the posterior longitudinal ligament after abrasion or mild injury to the posterior longitudinal ligament. Abrasion, scraping, or small cuts in the posterior longitudinal ligament stimulate the posterior longitudinal ligament to heal. Cells can then migrate from the posterior longitudinal ligament to the mesh component as the posterior longitudinal ligament heals.

FIG. 6C is a cranial view of an axial cross section of through disc 51 and the embodiment of the invention drawn in FIG. 6B. Mesh component 62 is positioned between posterior longitudinal ligament 69 and the AF or between layers of anulus fibrosus 68. Projection 67 is inserted into defect 55. Enlarged ends of sutures 56 extend from widows or slits cut in posterior longitudinal ligament 69.

FIG. 6D is posterior view of a coronal cross section through a segment of the spine and the embodiment of the invention drawn in FIG. 6C. The enlarged ends of sutures 56 were placed into holes drilled into vertebrae 50, 52. Cement was injected into the holes after inserting the sutures into the holes. Although the drawing shows four holes an alternative number of holes could be used to fasten the device to the spine. For example, two, three, five or more holes could be used to fasten the device to the spine. Similarly, two, three, five, six, or more anchors could be used to fasten the device to the spine. Although the drawings show the ends of four sutures projecting from the holes an alternative number of sutures could be used to fasten the device to the spine. For example, two, three, five, or more sutures could be used to fasten the device to the spine. Additionally, although the drawings show a single end of each suture projecting from the holes, both ends of each suture could project from the holes. For example, the sutures could be fastened to the spine with suture anchors that have an eyelet in the head of the anchor that is adapted to receive a suture therethrough. With these anchors, both ends of the sutures pass from the anchor and therefore, both ends of the suture could extend from the anchor. For example, eight ends of four sutures would project from four anchors used in the embodiment of the invention drawn in FIG. 5A. Additionally, two or more sutures may be placed in the eyelets of the suture anchors. Therefore, sixteen ends of eight sutures could project from four prior anchors (with two sutures per anchor) used in the embodiment of the invention drawn in FIG. 5A. The side portions of mesh component 62 are covered by posterior longitudinal ligament 69. The middle portion of mesh component 62 can be covered by anti-adhesion component 64 once it is expanded.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A device for fixing a defect in an anulus fibrosus adjacent a vertebral body of a patient, the defect defining a height dimension and left to right dimension, the device comprising:
   a mesh patch having a first and second layer defining a tube with a lumen therethrough;
   the lumen of the tube being oriented in a left to right direction relative to the defect in the annulus fibrosus;
   a suture having a first end, a middle portion, and a second end, wherein the middle portion of the suture is positioned between the first and second layers of the mesh patch;
   one or more bone anchors separate from the suture material; and
   wherein the mesh patch is positioned adjacent the defect in the annulus fibrosus with the first and second ends of the suture anchored to an adjacent vertebral body with the bones anchors so as to occlude the defect.

2. The device of claim 1, wherein the length of the tube is longer than the lateral dimension of the defect in the annulus fibrosus.

3. The device of claim 1, wherein:
the first and second layers both have cranial and caudal edges; and
the tube is formed by connected the cranial and caudal edges of the layers.

4. The device of claim 1, wherein the length of the tube is longer than the lateral dimension of the defect in the annulus fibrosus.

5. The device of claim 1, wherein the suture anchor is bone screw having an eyelet or a hook to which an end of the suture material attaches.

6. The device of claim 1, wherein the suture anchor is formed by drilling a hole into an adjacent vertebral body, inserting an end of the suture material into the hole, and filling the hole with curing material.

* * * * *